United States Patent [19]

Winkelmann et al.

[11] 3,984,426

[45] Oct. 5, 1976

[54] (1-ALKYL-5-NITRO-IMIDAZOLYL-2-ALKYL)-HETEROARYL COMPOUNDS

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[22] Filed: Nov. 27, 1974

[21] Appl. No.: 527,705

[30] Foreign Application Priority Data

Dec. 1, 1973 Germany............................ 2359922

[52] U.S. Cl........................ 260/302 H; 260/307 R; 260/307 G; 260/309; 424/270; 424/272
[51] Int. Cl.²................ C07D 413/00; C07D 417/00
[58] Field of Search........ 260/302 H, 307 R, 307 G; 424/270, 272

[56] References Cited

UNITED STATES PATENTS

| | | | |
|---|---|---|---|
| 3,813,401 | 5/1974 | Hughes et al. | 260/302 H |
| 3,853,893 | 12/1974 | Narayanan et al. | 260/307 R |

*Primary Examiner*—R. J. Gallagher
*Attorney, Agent, or Firm*—Curtis, Morris & Safford

[57] ABSTRACT

(1-alkyl-5-nitro-imidazolyl-2-alkyl)-heteroaryl compounds and a process for their manufacture are described. The new compounds are well compatible and are effective against bacteria and protozoa as well as against fungi. They are especially active against trichomonads and amebae.

8 Claims, No Drawings

(1-ALKYL-5-NITRO-IMIDAZOLYL-2-ALKYL)-HETEROARYL COMPOUNDS

The present invention relates to (1-alkyl-5-nitro-imidazolyl-2-alkyl)-heteroaryl compounds and to a process for preparing them.

It is known to use 1-(2-hydroxyethyl)-2-methyl-5-nitroimidazole (Metronidazol) for the treatment of protozoal diseases, such as trichomoniasis and amebiasis.

Object of this invention are (1-alkyl-5-nitro-imidazolyl-2-alkyl)-heteroaryl sulfides, sulfoxides and sulfones of the formula I

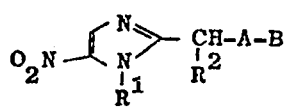   (I)

in which $R^1$ stands for a methyl or ethyl group, $R^2$ for a hydrogen atom or a methyl group, A for a sulfur bridge (—S—), a sulfoxide group (—SO—) or a sulfone group (—SO$_2$—) and B for

| | |
|---|---|
| an oxazole ring 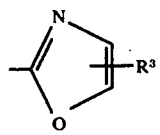 | a thiazole ring 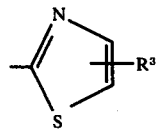 |
| an oxadiazole ring 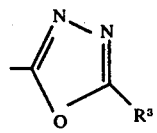 | a thiadiazole ring 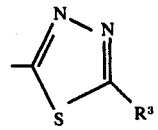 |
| an oxatriazole ring 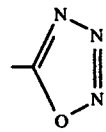 | a thiatriazole ring 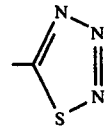 | which can be linked in the said manner to the sulfur bridge, sulfoxide group or sulfone group, and in which $R^3$ stands for a hydrogen atom, a methyl group, a cyano group, a nitro group or an amino group.

The new compounds are effective against various protozoa, in particular against trichomonads and amebae, as well as against trypanosoma and bacteria.

Further object of this invention is a process for the manufacture of (1-alkyl-5-nitro-imidazolyl-2-alkyl)-heteroaryl sulfides, sulfoxides and sulfones of the above-said formula I, which comprises a. reacting a 1-alkyl-2-alkyl-5-nitro-imidazole of the formula II

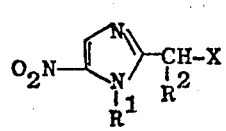   (II)

in which $R^1$ and $R^2$ are defined as above, and X stands for a halogen atom or an acyloxy group, preferably acetoxy, propoxy, butoxy, benzoyloxy, benzyloxy or tolyloxy, or an arylsulfonic acid ester group, preferably a benzene-sulfonic acid ester group, a toluenesulfonic acid ester group or a naphthalene-sulfonic acid ester group, with a heteroaryl mercaptan or the alkali metal or ammonium salt thereof corresponding to the formula III $$Y - S - B \qquad (III)$$

in which Y stands for hydrogen, an alkali metal, especially sodium or potassium, or ammonium and B is defined as above, or b. reacting a 1-alkyl-2-mercapto-alkyl-5-nitro-imidazole of the formula IV

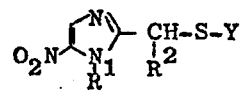   (IV)

in which $R^1$, $R^2$ and Y are defined as above, with a heteroaryl compound of the formula V $$X - B \qquad (V)$$

in which X and B are defined as above, and where required oxidizing the sulfide compounds of formula I thus obtained to yield a sulfoxide or sulfone.

As starting substances of formula II, there are mentioned for example 1-methyl-, 1-ethyl-2-chloro-, -2-bromo-, -2-iodo-methyl- or 1-methyl-, 1-ethyl-2-chloro-, -2-bromo-, -2-iodo-(1-ethyl)-5-nitro-imidazole, 1-methyl- or 1-ethyl-2-acetoxy-5-nitro-imidazole, or 1-methyl- or 1-ethyl-2-benzene- or -2-toluene-sulfonic acid ester.

As starting substances of formula III, there are mentioned for example 2-mercapto-oxazole-1,3, -thiazole-1,3, -oxadiazole-1,3,4, -thiadiazole-1,3,4,5-mercapto-oxatriazole-1,2,3,4, -thiatriazole-1,2,3,4, 4- or 5-methyl-, -cyano-, -nitro- or -amino-2-mercapto-oxazole-1,3, 4- or 5-methyl-, cyano-, -nitro- or -amino-2-mercapto-thiazole-1,3 5-methyl-, -cyano-, -nitro- or -amino-oxadiazole-1,3,4, 5-methyl-, -cyano-, -nitro- or -amino-thiadiazole-1,3,4.

Instead of the said mercapto compounds, the alkali metal or ammonium salts thereof, or mercaptan-yielding substances such as, for example, isothiouronium salts, may also be used.

As starting substances of formula IV, there are mentioned for example 1-methyl-, 1-ethyl-2-mercapto-methyl- or 1-methyl-, 1-ethyl-2-mercapto-(1-ethyl)-5-nitro-imidazoles or the alkali metal or ammonium salts thereof, or mercapto-yielding agents such as, for example, isothiouronium salts.

As starting compounds of formula V, there are mentioned for example all the compounds as mentioned for formula III, wherein, however, the mercapto group is replaced by a halogen atoms, for example a fluorine, chlorine, bromine or iodine atom, or an acetoxy- or benzene- or toluene-sulfonic acid ester grouping.

The 1-alkyl-2-chloroalkyl-nitro-imidazoles of formula II, used as starting compounds, are obtained by reacting 1-alkyl-2-hydroxy-alkyl-5-nitro-imidazoles with thionyl chloride and can be converted, where required, into fluorinated, brominated or iodinated compounds by a reaction with the corresponding metal halides.

The 1-alkyl-2-acyloxy-alkyl-5-nitro-imidazoles or 1-alkyl-2-(arylsulfonyloxy-alkyl)-5-nitro-imidazoles of formula II, also used as starting compounds, are obtained by reacting 1-alkyl-2-hydroxyalkyl-5-nitro-imidazoles with an acid anhydride or chloride, such as acetic anhydride or acetyl chloride, or with an arylsulfonic acid chloride, such as 4-toluene-sulfonic acid chloride.

The mercapto-heterocyclic compounds of formula III used as starting compounds are prepared by reacting corresponding halogeno-heterocyclic compounds with hydrogen sulfide or, in the case of cyano-heterocyclic compounds, by diazotizing the corresponding amino-cyano-heterocyclic compounds and reacting the diazonium salt thus obtained with alkali metal xanthogenates.

The 1-alkyl-2-mercapto-alkyl-5-nitro-imidazoles of formula IV used as starting substances are obtained by reacting corresponding 1-alkyl-2-halogeno-alkyl-5-nitro-imidazoles with hydrogen sulfide.

The halogeno- or acyloxy-heterocyclic compounds of formula V used as starting substances are prepared by reacting the corresponding hydroxy compounds with phosphorus halides or an acyl chloride.

The two variants (a) and (b) of the process of the invention are advantageously carried out using equimolar amounts of each starting substance, advantageously in a solvent or dispersing agent. When the free mercapto compounds of formula III or IV are used, the solvent used is preferably a polar one; when the salts thereof are used, the solvent chosen is preferably a non-polar one.

As non polar solvents, there are mentioned, for example benzene, toluene, xylene or chlorobenzene. As polar solvents, there are mentioned, for example, alcohols, such as methanol, ethanol, propanol, butanol, methoxy-ethanol, or ketones, such as acetone, methylethyl-ketone, methylbutyl-ketone; further pyridine, picoline, quinoline, dimethylformamide, dimethylacetamide, N-methyl-pyrrolidone, tetramethyl-urea, hexamethylphosphoric acid triamide or dimethyl-sulfoxide.

The reaction temperatures may generally range from 0° to 130°C, preferably from 20° to 80°C. In this connection, the reactions using polar solvents may be carried out at lower temperatures, those using non-polar solvents suitably at elevated temperatures. Depending on the temperatures chosen, the reaction times range from a few minutes to several hours.

When the free mercapto compounds of formulae III and IV are used, it is advisable to use an acid-binding agent, such as as base, for example, triethylamine or pyridine, as well as alkali metal or alkaline earth metal carbonates and bicarbonates, hydroxides and alkoxides, for example the methoxides, ethoxides and butoxides.

The products of the invention are isolated according to the usual methods, for example by distilling off the solvents used or diluting the reaction solution with water. Where required, they may be purified by recrystallizing them from a mixture of appropriate solvents.

The sulfides of formula I (A = —S—), obtained according to one of the above-said process variants (a) or (b), may be converted by oxidation into the corresponding sulfoxides (A = —SO—) or sulfones (A = —SO$_2$—).

The oxidation reactions are advantageously carried out using simple or double molar amounts of an oxidizing agent. The treatment of the sulfides with one mol-equivalent of the oxidizing agent yields sulfoxides, with two mol-equivalents of oxidizing agent, it yields sulfones. As oxidizing agents, there may be used, for example hydrogen peroxide, or per-acids, such as peracetic acid, per-trifluoroacetic acid or metachloroperbenzoic acid, as well as nitric acid or chromic acid, or the salts thereof; moreover permanganates, hypochlorites, perchlorates, periodates and nitrogen oxides. The oxidation reactions are advantageously carried out in a solvent or dispersing agent.

For this purpose, those solvents are particularly useful which are not attacked by the oxidizing agent, for example acetic acid, or trifluoroacetic acid. When perbenzoic acid is used, methylene chloride or chloroform are also useful as solvents.

The oxidation reactions which are to yield sulfoxides are generally carried out at temperatures ranging from 10° to 30°C. The sulfones are generally obtained at oxidation temperatures of from 50° to 100°C. The sulfonyl compounds may be also prepared, where required by oxidation of the corresponding sulfonyl compounds by means of the specified oxidizing agents at elevated temperatures.

Depending on the temperature chosen and on the desired end product, the oxidation times range from a few minutes to some hours.

The products of the invention are isolated either by diluting the reaction solution with water and, at the same time, precipitating them or by evaporating the organic solvent in vacuo. They may also be purified, where required, by recrystallizing them from a suitable solvent or mixture of solvents.

The new compounds of formula I are well compatible and are effective against pathogens, such as bacteria and protozoa as well as against fungi. They are especially active against trichomonads and amebae and are herein superior to the known Metronidazol. The individual dosage unit ranges from 5 to 100 mg/kg of body weight.

The new compounds of formula I are therefore suitable for the treatment of protozoal diseases in mammals as caused, for example by infections with *Trichomonas vaginalis* and *Entamoeba histolytica*, as well as with *trypanosoma cruci*, *trypanosoma bruci* and *trypanosoma congolense*.

The compounds of the invention can be administered orally or locally. The dosage unit forms for oral administration are usually tablets or capsules containing, per daily dosage unit, about 10 to 750 mg, preferably 150 to 500 mg, of the active substance in combination with a usual additive as diluent and/or extender. For local application, powders, jellies, creams, ointments or suppositories are useful.

The following Examples illustrate the invention.

EXAMPLES

1.

1-Methyl-2-(1,3-thiazolyl-2-thiomethyl)-5-nitro-imidazole 2.3 Grams (0.1 mol) of metallic sodium were dissolved in small portions in 50 ml of anhydrous methanol. In this sodium methylate solution, 11.7 g (0.1 mol) of 2-mercapto-1,3-thiazole as a solution in 70 ml of anhydrous methanol were introduced and the solution was concentrated by evaporation under reduced pressure. The residue was combined with a solution of 17.55 g (0.1 mol) of 1-methyl-2-chloromethyl-5-nitro-imidazole in 100 ml of dimethylacetamide, and the reaction mixture was heated to 110°C for 1 hour. After cooling, water was added to the solution until crystallization set in. The end product was filtered off and recrystallized from ethanol while charcoal was added.

In this manner, 18.5 g of 1-methyl-2-(1,3-thiazolyl-2-thiomethyl)-5-nitro-imidazole (corresponding to 72 % of the theoretical yield) were obtained in the form of yellowish crystals, m.p. 84°C.

In the same manner, the following compounds were obtained in good yields:

2. 1-methyl-2-(1,3,4-thiadiazolyl-2-thiomethyl)-5-nitro-imidazole, melting point of 106°C, from 1-methyl-2-chloromethyl-5-nitro-imidazole and 2-mercapto-1,3,4-thiadiazole;
3. 1-methyl-2-(5-methyl-1,3-oxazolyl-2-thiomethyl)-5-nitro-imidazole, melting point 95°C, from 1-methyl-2-chloromethyl-5-nitro-imidazole and 2-mercapto-5-methyl-1,3-oxazole;
4. 1-methyl-2-(5-methyl-1,3-thiazolyl-2-thiomethyl)-5-nitro-imidazole, melting point 79°C, from 1-methyl-2-chloromethyl-5-nitro-imidazole and 2-mercapto-5-methyl-1,3-thiazole;
5. 1-methyl-2-(5-cyano-1,3-thiazolyl-2-thiomethyl)-5-nitro-imidazole, melting point 185°–187°C, from 1-methyl-2-chloro-methyl-5-nitro-imidazole and 2-mercapto-5-cyano-1,3-thiazole;
6. 1-methyl-2-(5-nitro-1,3-thiazolyl-2-thiomethyl)-5-nitro-imidazole, m.p. 160°C, from 1-methyl-2-chloromethyl-5-nitro-imidazole and 2-mercapto-5-nitro-1,3-thiazole;
7. 1-methyl-2-(5-methyl-1,3,4-oxadiazolyl-2-thiomethyl)-5-nitro-imidazole, m.p. 142°C, from 1-methyl-2-chloromethyl-5-nitro-imidazole and 2-mercapto-5-methyl-1,3,4-oxadiazole;
8. 1-methyl-2-(5-methyl-1,3,4-thiadiazolyl-2-thiomethyl)-5-nitro-imidazole, m.p. 129°C, from 1-methyl-2-chloromethyl-5-nitro-imidazole and 2-mercapto-5-methyl-1,3,4-thiadiazole;
9. 1-methyl-2-(5-amino-1,3,4-thiadiazolyl-2-thiomethyl)-5-nitro-imidazole, m.p. 176°C, from 1-methyl-2-chloro-methyl-5-nitro-imidazole and 2-mercapto-5-amino-1,3,4-thiadiazole;
10. 1-ethyl-2-(5-nitro-1,3-thiazolyl-2-thiomethyl)-5-nitro-imidazole, m.p. 85°–88°C, from 1-ethyl-2-chloromethyl-5-nitro-imidazole and 2-mercapto-1,3-thiazole;
11. 1-methyl-2-(5-nitro-1,3-thiazolyl-2-thioethyl)-5-nitro-imidazole, m.p. 80°–82°C, from 1-methyl-2-chloro-(1-ethyl)-5-nitro-imidazole and 2-mercapto-1,3-thiazole;
12. 1-methyl-2-(1,3-oxazolyl-2-thiomethyl)-5-nitro-imidazole;
13. 1-methyl-2-(1,3,4-oxadiazolyl-2-thiomethyl)-5-nitro-imidazole;
14. 1-methyl-2-(1,2,3,4-oxatriazolyl-5-thiomethyl)-5-nitro-imidazole;
15. 1-methyl-2-(1,2,3,4-thiatriazolyl-5-thiomethyl)-5-nitro-imidazole;
16. 1-methyl-2-(5-amino-1,3-oxazolyl-2-thiomethyl)-5-nitro-imidazole;
17. 1-methyl-2-(5-cyano-1,3-oxazolyl-2-thiomethyl)-5-nitro-imidazole;
18. 1-methyl-2-(5-nitro-1,3-oxazolyl-2-thiomethyl)-5-nitro-imidazole;
19. 1-methyl-2-(5-amino-1,3-thiazolyl-2-thiomethyl)-5-nitro-imidazole;
20. 1-methyl-2-(5-amino-1,3,4-oxadiazolyl-2-thiomethyl)-5-nitro-imidazole;
21. 1-methyl-2-(5-cyano-1,3,4-oxadiazolyl-2-thiomethyl)-5-nitro-imidazole;
22. 1-methyl-2-(5-nitro-1,3,4-oxadiazolyl-2-thiomethyl)-5-nitro-imidazole;
23. 1-methyl-2-(5-cyano-1,3,4-thiadiazolyl-2-thiomethyl)-5-nitro-imidazole;
24. 1-methyl-2-(5-nitro-1,3,4-thiadiazolyl-2-thiomethyl)-5-nitro-imidazole;
25. 1-ethyl-2-(1,3-oxazolyl-2-thiomethyl)-5-nitro-imidazole;
26. 1-ethyl-2-(1,3-thiazolyl-2-thiomethyl)-5-nitro-imidazole;
27. 1-ethyl-2-(1,3,4-oxadiazolyl-2-thiomethyl)-5-nitro-imidazole;
28. 1-ethyl-2-(1,3,4-thiadiazolyl-2-thiomethyl)-5-nitro-imidazole;
29. 1-ethyl-2-(1,2,3,4-oxatriazolyl-5-thiomethyl)-5-nitro-imidazole;
30. 1-ethyl-2-(1,2,3,4-thiatriazolyl-5-thiomethyl)-5-nitro-imidazole;
31. 1-ethyl-2-(5-methyl-1,3-oxazolyl-2-thiomethyl)-5-nitro-imidazole;
32. 1-ethyl-2-(5-amino-1,3-oxazolyl-2-thiomethyl)-5-nitro-imidazole;
33. 1-ethyl-2-(5-cyano-1,3-oxazolyl-2-thiomethyl)-5-nitro-imidazole;
34. 1-ethyl-2-(5-nitro-1,3-oxazolyl-2-thiomethyl)-5-nitro-imidazole;
35. 1-ethyl-2-(5-methyl-1,3-thiazolyl-2-thiomethyl)-5-nitro-imidazole;
36. 1-ethyl-2-(5-amino-1,3-thiazolyl-2-thiomethyl)-5-nitro-imidazole;
37. 1-ethyl-2-(5-cyano-1,3-thiazolyl-2-thiomethyl)-5-nitro-imidazole;
38. 1-ethyl-2-(5-methyl-1,3,4-oxadiazolyl-2-thiomethyl)-5-nitro-imidazole;
39. 1-ethyl-2-(5-amino-1,3,4-oxadiazolyl-2-thiomethyl)-5-nitro-imidazole;
40. 1-ethyl-2-(5-cyano-1,3,4-oxadiazolyl-2-thiomethyl)-5-nitro-imidazole;
41. 1-ethyl-2-(5-nitro-1,3,4-oxadiazolyl-2-(5-nitro-imidazole;
42. 1-ethyl-2-(5-methyl-1,3,4-thiadiazolyl-2-thiomethyl)-5-nitro-imidazole;

43. 1-ethyl-2-(5-amino-1,3,4-thiadiazolyl-2-thiomethyl)-5-nitro-imidazole;
44. 1-ethyl-2-(5-cyano-1,3,4-thiadiazolyl-2-thiomethyl)-5-nitro-imidazole;
45. 1-ethyl-2-(5-nitro-1,3,4-thiadiazolyl-2-thiomethyl)-5-nitro-imidazole;
46. 1-methyl-2-[1,3-oxazolyl-2-thio-(1-ethyl)]-5-nitro-imidazole;
47. 1-methyl-2-[1,3-thiazolyl-2-thio-(1-ethyl)]-5-nitro-imidazole;
48. 1-methyl-2-[1,3,4-oxadiazolyl-2-thio-(1-ethyl)]-5-nitro-imidazole;
49. 1-methyl-2-[1,3,4-thiadiazolyl-2-thio-(1-ethyl)]-5-nitro-imidazole;
50. 1-methyl-2-[1,2,3,4-oxatriazolyl-5-thio-(1-ethyl)]-5-nitro-imidazole;
51. 1-methyl-2-[1,2,3,4-thiatriazolyl-5-thio-(1-ethyl)]-5-nitro-imidazole;
52. 1-methyl-2-[5-methyl-1,3-oxazolyl-2-thio-(1-ethyl)]-5-nitro-imidazole;
53. 1-methyl-2-[5-amino-1,3-oxazolyl-2-thio-(1-ethyl)]-5-nitro-imidazole;
54. 1-methyl-2-[5-cyano-1,3-oxazolyl-2-thio-(1-ethyl)]-5-nitro-imidazole;
55. 1-methyl-2-[5-nitro-1,3-oxazolyl-2-thio-(1-ethyl)]-5-nitro-imidazole;
56. 1-methyl-2-[5methyl-1,3-thiazolyl-2-thio-(1-ethyl)]-5-nitro-imidazole;
57. 1-methyl-2-[5-amino-1,3-thiazolyl-2-thio-(1-ethyl)]-5-nitro-imidazole;
58. 1-methyl-2-[5-cyano-1,3-thiazolyl-2-thio-(1-ethyl)]-5-nitro-imidazole;
59. 1-methyl-2-[5-methyl-1,3,4-oxadiazolyl-2-thio-(1-ethyl)]-5-nitro-imidazole;
60. 1-methyl-2-[5-amino-1,3,4-oxadiazolyl-2-thio-(1-ethyl)]-5-nitro-imidazole;
61. 1-methyl-2-[5-cyano-1,3,4-oxadiazolyl-2-thio-(1-ethyl)]-5-nitro-imidazole;
62. 1-methyl-2-[5-nitro-1,3,4-oxadiazolyl-2-thio-(1-ethyl)]-5-nitro-imidazole;
63. 1-methyl-2-[5-methyl-1,3,4-thiadiazolyl-2-thio-(1-ethyl)]-5-nitro-imidazole;
64. 1-methyl-2-[5-amino-1,3,4-thiadiazolyl-2-thio-(1-ethyl)]-5-nitro-imidazole;
65. 1-methyl-2-[5-cyano-1,3,4-thiadiazolyl-2-thio-(1-ethyl)]-5-nitro-imidazole and
66. 1-methyl-2-[5-nitro-1,3,4-thiadiazolyl-2-thio-(1-ethyl)]-5-nitro-imidazole.

67.
1-Methyl-2-(1,3-thiazolyl-2-sulfinylmethyl)-5-nitro-imidazole 25.6 Grams (0.1 mol) of 1-methyl-2-(1,3-thiazolyl-2-thiomethyl)-5-nitro-imidazole were dissolved in 200 ml of chloroform, and 17.25 g (0.1 mol) of m-chloroperbenzoic acid dissolved in 50 ml of chloroform were added dropwise while stirring at room temperature. The reaction solution was then stirred for another hour at room temperature, shaken out with dilute sodium carbonate solution, the chloroform phase was separated, the remaining solution was dried over sodium sulfate and evaporated. The residue was recrystallized from alcohol.

Thus, 19.1 g of 1-methyl-2-(1,3-thiazolyl-2-sulfinylmethyl)-5-nitro-imidazole (corresponding to 70 % of the theoretical yield) were obtained in the form of yellowish crystals, melting point 98°C.

In the same manner, the following compounds were obtained in good yields from the corresponding thio compounds:
68. 1-methyl-2-(1,3-oxazolyl-2-sulfinylmethyl)-5-nitro-imidazole;
69. 1-methyl-2-(1,3,4-oxadiazolyl-2-sulfinylmethyl)-5-nitro-imidazole;
70. 1-methyl-2-(1,3,4-thiadiazolyl-2-sulfinylmethyl)-5-nitro-imidazole;
71. 1-methyl-2-(1,2,3,4-oxatriazolyl-5-sulfinylmethyl)-5-nitro-imidazole;
72. 1-methyl-2-(1,2,3,4-thiatriazolyl-5-sulfinylmethyl)-5-nitro-imidazole;
73. 1-methyl-2-(5-methyl-1,3-oxazolyl-2-sulfinylmethyl)-5-nitro-imidazole;
74. 1-methyl-2-(5-methyl-1,3-thiazolyl-2-sulfinylmethyl)-5-nitro-imidazole;
75. 1-methyl-2-(5-methyl-1,3,4-oxadiazolyl-2-sulfinylmethyl)-5-nitro-imidazole;
76. 1-methyl-2-(5-methyl-1,3,4-thiadiazolyl-2-sulfinylmethyl)-5-nitro-imidazole;
77. 1-ethyl-2-(1,3-oxazolyl-2-sulfinylmethyl)-5-nitro-imidazole;
78. 1-ethyl-2-(1,3-thiazolyl-2-sulfinylmethyl)-5-nitro-imidazole;
79. 1-ethyl-2-(1,3,4-oxadiazolyl-2-sulfinylmethyl)-5-nitro-imidazole;
80. 1-ethyl-2-(1,3,4-thiadiazolyl-2-sulfinylmethyl)-5-nitro-imidazole;
81. 1-ethyl-2-(1,2,3,4-oxatriazolyl-5-sulfinylmethyl)-5-nitro-imidazole;
82. 1-ethyl-2-(1,2,3,4-thiatriazolyl-5-sulfinylmethyl)-5-nitro-imidazole;
83. 1-ethyl-2-(5-methyl-1,3-oxazolyl-2-sulfinylmethyl)-5-nitro-imidazole;
84. 1-ethyl-2-(5-methyl-1,3-thiazolyl-2-sulfinylmethyl)-5-nitro-imidazole;
85. 1-ethyl-2-(5-methyl-1,3,4-oxadiazolyl-2-sulfinylmethyl)-5-nitro-imidazole;
86. 1-ethyl-2-(5-methyl-1,3,4-thiadiazolyl-2-sulfinylmethyl)-5-nitro-imidazole;
87. 1-methyl-2-[1,3-oxazolyl-2-sulfinyl-(1-ethyl)]-5-nitro-imidazole;
88. 1-methyl-2-[1,3-thiazolyl-2-sulfinyl-(1-ethyl)]-5-nitro-imidazole;
89. 1-methyl-2-[1,3,4-oxadiazolyl-2-sulfinyl-(1-ethyl)]-5-nitro-imidazole;
90. 1-methyl-2-[1,3,4-thiadiazolyl-2-sulfinyl-(1-ethyl)]-5-nitro-imidazole;
91. 1-methyl-2-[1,2,3,4-oxatriazolyl-5-sulfinyl-(1-ethyl)]-5-nitro-imidazole;
92. 1-methyl-2-[1,2,3,4-thiatriazolyl-5-sulfinyl-(1-ethyl)]-5-nitro-imidazole;
93. 1-methyl-2-[5-methyl-1,3-oxazolyl-2-sulfinyl-(1-ethyl)]-5-nitro-imidazole;
94. 1-methyl-2-[5-methyl-1,3-thiazolyl-2-sulfinyl-(1-ethyl)]-5-nitro-imidazole;
95. 1-methyl-2-[5-methyl-1,3,4-oxadiazolyl-2-sulfinyl-(1-ethyl)]-5 -nitro-imidazole and
96. 1-methyl-2-[5-methyl-1,3,4-thiadiazolyl-2-sulfinyl-(1-ethyl)]-5-nitro-imidazole.

97.
1-Methyl-2-(1,3-thiazolyl-2-sulfonylmethyl)-5-nitro-imidazole 25.6 Grams (0.1 mol) of 1-methyl-2-(1,3-thiazolyl-2-thiomethyl)-5-nitro-imidazole were dissolved in 400 ml of glacial acetic acid, and 20.0 ml (0.2 mol) of 35 % hydrogen peroxide were added dropwise while stirring at room temperature. The reaction was not exothermic. Stirring was then continued for 2 hours while heating on a steam bath. The reaction solution was concentrated by evaporation under reduced pressure and the residue was recrystallized from water/alcohol.

Thus, 21.6 g of 1-methyl-2-1,3-thiazolyl-2-sulfonylmethyl)-5-nitro-imidazole (corresponding to 75 % of the theoretical yield) were obtained in the form of yellowish crystals, melting point 126°C.

In the same manner, the following compounds were obtained in good yields from the corresponding thio compounds:

98. 1-methyl-2-(1,3-oxazolyl-2-sulfonylmethyl)-5-nitro-imidazole;
99. 1-methyl-2-(1,3,4-oxadiazolyl-2-sulfonylmethyl)-5-nitro-imidazole;
100. 1-methyl-2-(1,3,4-thiadiazolyl-2-sulfonylmethyl)-5-nitro-imidazole;
101. 1-methyl-2-(1,2,3,4-oxatriazolyl-5-sulfonylmethyl)-5-nitro-imidazole;
102. 1-methyl-2-(1,2,3,4-thiatriazolyl-5-sulfonylmethyl)-5-nitro-imidazole;
103. 1-methyl-2-(5-methyl-1,3-oxazolyl-2-sulfonylmethyl)-5-nitro-imidazole;
104. 1-methyl-2-(5-methyl-1,3-thiazolyl-2-sulfonylmethyl)-5-nitro-imidazole;
105. 1-methyl-2-(5-methyl-1,3,4-oxadiazolyl-2-sulfonylmethyl)-5-nitro-imidazole;
106. 1-methyl-2-(5-methyl-1,3,4-thiadiazolyl-2-sulfonylmethyl)-5-nitro-imidazole;
107. 1-ethyl-2-(1,3-oxazolyl-2-sulfonylmethyl)-5-nitro-imidazole;
108. 1-ethyl-2-(1,3-thiazolyl-2-sulfonylmethyl)-5-nitro-imidazole;
109. 1-ethyl-2-(1,3,4-oxadiazolyl-2-sulfonylmethyl)-5-nitro-imidazole;
110. 1-ethyl-2-(1,3,4thiadiazolyl-2-sulfonylmethyl)-5-nitro-imidazole;
111. 1-ethyl-2-(1,2,3,4-oxatriazolyl-5-sulfonylmethyl)-5-nitro-imidazole;
112. 1-ethyl-2-(1,2,3,4-thiatriazolyl-5-sulfonylmethyl)-5-nitro-imidazole;
113. 1-ethyl-2-(5-methyl-1,3-oxazolyl-2-sulfonylmethyl)-5-nitro-imidazole;
114. 1-ethyl-2-(5-methyl-1,3-thiazolyl-2-sulfonylmethyl)-5-nitro-imidazole;
115. 1-ethyl-2-(5-methyl-1,3,4-oxadiazolyl-2-sulfonylmethyl)-5-nitro-imidazole;
116. 1-ethyl-2-(5-methyl-1,3,4-thiadiazolyl-2-sulfonylmethyl)-5-nitro-imidazole;
117. 1-methyl-2-[1,3-oxazolyl-2-sulfonyl-(1-ethyl)]-5-nitro-imidazole;
118. 1-methyl-2-[1,3-thiazolyl-2-sulfonyl-(1-ethyl)]-5-nitro-imidazole;
119. 1-methyl-2-[1,3,4-oxadiazolyl-2-sulfonyl-(1-ethyl)]-5-nitro-imidazole;
120. 1-methyl-2-[1,3,4-thiadiazolyl-2-sulfonyl-(1-ethyl)]-5-nitro-imidazole;
121. 2-methyl-2-[1,2,3,4-oxatriazolyl-5-sulfonyl-(1-ethyl)]-5-nitro-imidazole;
122. 1-methyl-2-[1,2,3,4-thiatriazolyl-5-sulfonyl-(1-ethyl)]-5-nitro-imidazole;
123. 1-methyl-2-[5-methyl-1,3-oxazolyl-2-sulfonyl-(1-ethyl)]-5-nitro-imidazole;
124. 1-methyl-2-[5-methyl-1,3-thiazolyl-2-sulfonyl-(1-ethyl)]-5-nitro-imidazole;
125. 1-methyl-2-[5-methyl-1,3,4-oxadiazolyl-2-sulfonyl-(1-ethyl)]-5-nitro-imidazole and
126. 1-methyl-2-[5-methyl-1,3,4-thiadiazolyl-2-sulfonyl-(1-ethyl]-5-nitro-imidazole.

127.
1-Methyl-2-(5-nitro-1,3-thiazolyl-2-thiomethyl)-5-nitro-imidazole 5.0 grams of 5-(1-methyl-5-nitro-imidazolyl-2-methyl)-isothio-uronium chloride (0.02 mol) were dissolved while stirring in 200 ml of methanol, and the solution was cooled to 0°C.

Under an atmosphere of nitrogen, a solution of 0.92 g of sodium metal in 20 ml of methanol was added dropwise at this temperature within about 5 minutes. Stirring was continued for 15 minutes at 0°C, whereupon the originally yellow solution took a yellow-orange color. A separately prepared solution of 4.2 g of 2-bromo-5-nitro-thiazole in 50 ml of methanol was then rapidly added dropwise. Care was taken that the reaction temperature did not exceed 0°C. Within a reaction time of 2 hours at 0° to +10°C, the solution took a red brown color, and a brown substance precipitated. This precipitate was suction-filtered, washed with water and methanol and recrystallized from isopropanol with an addition of charcoal.

Yield: 2.8 g ( = 47 % of the theory) of yellow ocre-colored crystals, melting point 160°C.

We claim:
1. A (1-alkyl-5-nitro-imidazolyl-2-alkyl)-heteroaryl sulfide, sulfoxide or sulfone of the formula

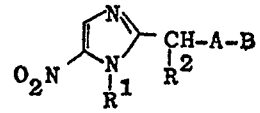

in which $R^1$ is methyl or ethyl, $R^2$ is hydrogen or methyl, A is a sulfur bridge (—S—), a sulfoxide group (—SO—) or a sulfone group (—SO$_2$—) and B is one of the following rings:

oxazole 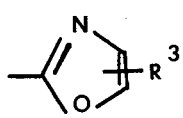

thiazole 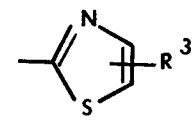

oxadiazole 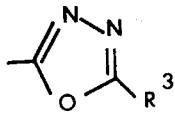

thiadiazole 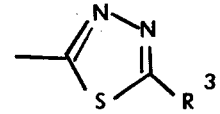

oxatriazole 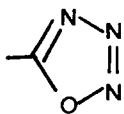 and thiatriazole 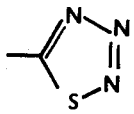

which may be linked in the manner indicated to the sulfur bridge, to the sulfoxide or sulfone group, and wherein $R^3$ is hydrogen, methyl, cyano, nitro or amino.

2. The compound of claim 1, which is 1-methyl-2-(1,3-thiazolyl-2-thiomethyl)-5-nitro-imidazole.

3. The compound of claim 1, which is 1-methyl-2-(1,3,4-thiadiazolyl-2-thiomethyl)-5-nitro-imidazole.

4. The compound of claim 1, which is 1-methyl-2-(5-methyl-1,3-thiazolyl-2-thiomethyl)-5-nitro-imidazole.

5. The compound of claim 1, which is 1-methyl-2-(5-nitro-1,3-thiazolyl-2-thiomethyl)-5-nitro-imidazole.

6. The compound of claim 1, which is 1-methyl-2-(5-methyl-1,3,4-oxadiazolyl-2-thiomethyl)-5-nitro-imidazole.

7. The compound of claim 1, which is 1-methyl-2-(5-methyl-1,3,4-thiadiazolyl-2-thiomethyl)-5-nitro-imidazole.

8. The compound of claim 1, which is 1-methyl-2-(5-amino-1,3,4-thiadiazolyl-2-thiomethyl)-5-nitro-imidazole.

* * * * *